United States Patent [19]
Depp

[11] Patent Number: 5,427,097
[45] Date of Patent: Jun. 27, 1995

[54] APPARATUS FOR AND METHOD OF CARRYING OUT STEREOTAXIC RADIOSURGERY AND RADIOTHERAPY

[75] Inventor: Joseph G. Depp, San Jose, Calif.
[73] Assignee: Accuray, Inc., Santa Clara, Calif.
[21] Appl. No.: 989,045
[22] Filed: Dec. 10, 1992
[51] Int. Cl.⁶ ............................................. A61B 5/05
[52] U.S. Cl. ................................. 128/653.1; 606/130
[58] Field of Search ....................... 364/413.24, 413.25, 364/413.26; 378/195, 196, 197, 198, 205, 208, 65, 17; 128/653.1, 660.01, 660.08, 660.09, 660.1, 906; 606/130

[56] References Cited

U.S. PATENT DOCUMENTS

| | | |
|---|---|---|
| 4,118,631 | 10/1978 | Froggatt . |
| 4,233,519 | 11/1980 | Coad . |
| 4,583,537 | 4/1986 | Derechinsky et al. ............. 606/130 |
| 4,605,012 | 8/1986 | Ringeisen et al. ........... 128/653.1 X |
| 4,633,494 | 12/1986 | Klausz . |
| 4,741,008 | 4/1988 | Franke . |
| 4,791,934 | 12/1988 | Brunnett . |
| 4,846,173 | 7/1989 | Davidson . |
| 4,868,843 | 9/1989 | Nunan . |
| 4,998,268 | 3/1991 | Winter . |
| 5,027,818 | 7/1991 | Bova et al. ....................... 128/653.1 |
| 5,037,374 | 8/1991 | Carol ................................ 378/65 X |
| 5,078,140 | 1/1992 | Kwoh ............................... 128/653.1 |
| 5,107,839 | 4/1992 | Houdek et al. .................. 128/653.1 |
| 5,160,337 | 11/1992 | Cosman ........................... 378/17 X |
| 5,186,174 | 2/1993 | Schlondorff et al. ............ 128/653.1 |
| 5,205,289 | 4/1993 | Hardy et al. .................... 128/653.1 |
| 5,207,223 | 5/1993 | Adler ............................... 606/130 X |
| 5,230,338 | 7/1993 | Allen et al. ..................... 606/130 X |

OTHER PUBLICATIONS

Friets et al. "A Frameless Stereotaxic Operating Microscope for Neurosurgery" Jun. 1989, pp. 608–616 IEE Transactions.

Primary Examiner—Lee S. Cohen
Assistant Examiner—Samuel Gilbert
Attorney, Agent, or Firm—Gray, Cary, Ware and Freidenrich

[57] ABSTRACT

There is disclosed herein a technique for carrying out stereotaxic radiosurgery or radiotherapy on a particular target region within a patient by a radiosurgical/radiotherapeutic beam of radiation which is at least intermittently directed along a beam path through the target region. One particular beam generating arrangement illustrated is carried by a robotic arm which is movable in at least three dimensions. In accordance with one embodiment disclosed herein, a method and apparatus are provided for moving the robotic arm and beam generating arrangement along a predetermined, non-circular and non-linear path transverse to the beam path while, at the same time, the beam path is directed into the target region. In this way, the radiosurgical/radiotherapeutic beam can be directed through the target region from particular treatment points along the transverse path so as to define a non-spherical target region. In accordance with a second embodiment, the apparatus disclosed herein includes an emergency stop arrangement separate from and independent of the controlling the robotic arm controller for automatically stopping all movement of the robotic arm and turning off the beam if the robotic arm deviates from its intended transverse path. In a third embodiment, the apparatus utilizes a plurality of target locating beams of radiation apart from but cooperating with the radiosurgical/radiotherapeutic beam to accurately and continuously locate the target region in substantially real time.

24 Claims, 6 Drawing Sheets

SYSTEM BLOCK DIAGRAM

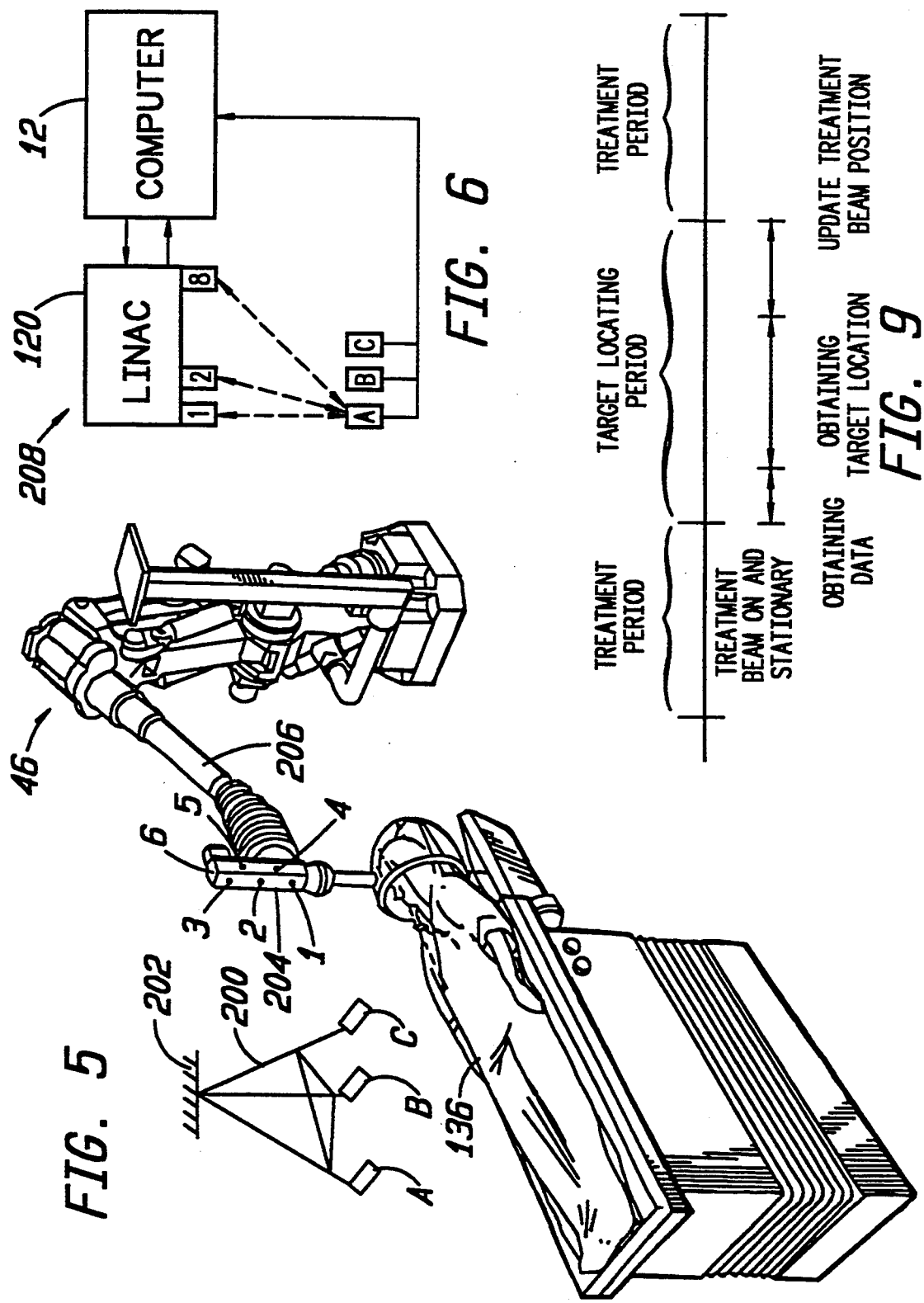

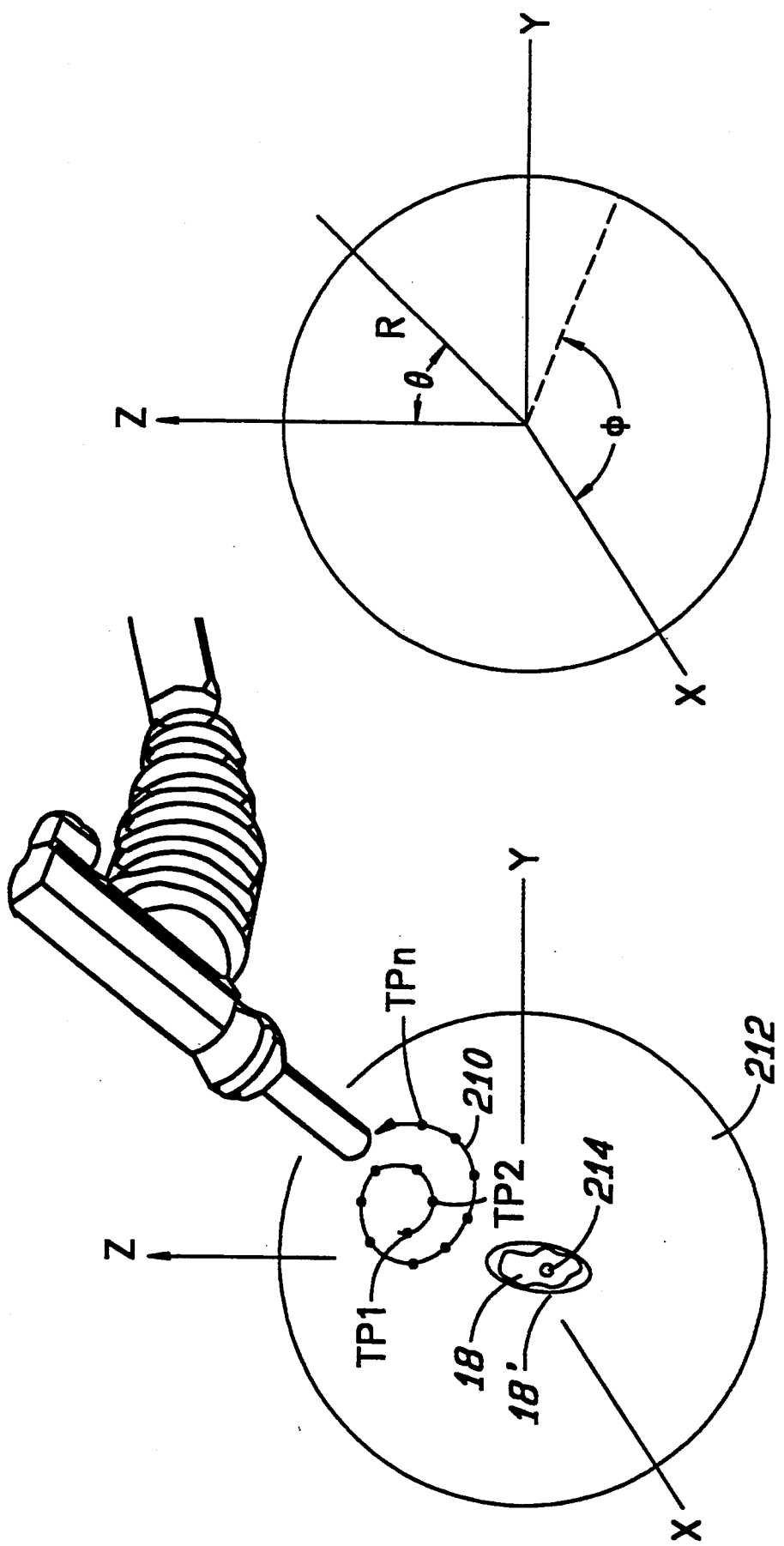

APPARATUS FOR AND METHOD OF CARRYING OUT STEREOTAXIC RADIOSURGERY AND RADIOTHERAPY

The present invention relates generally to an apparatus for and method of carrying out stereotaxic radiosurgery and/or radiotherapy on a particular target region within a patient utilizing previously obtained reference data indicating the position of the target region with respect to its surrounding area which also contains certain nearby reference points. The present invention relates more particularly to a number of improvements to the method and apparatus disclosed in copending U.S. patent application Ser. No. 07/600,501 in the name of John R. Adler, filed Oct. 19, 1990, which application is incorporated herein by reference.

The term stereotaxic radiosurgery refers to a procedure in which a beam of radiation is used to render a target region, that is, a particular volume of tissue, specifically tumorous tissue, necrotic, as is well known. Typically, this requires in the neighborhood of 2000 to 3000 rads of radiation. The term stereotaxic radiotherapy refers to a procedure in which a beam of radiation is applied to the target region for therapeutic, non-necrotic purposes. The amount of radiation typically utilized in this latter case is an order of magnitude less than a necrotic dose, for example between 200 and 300 rads of radiation. By target region is meant a specific volume of particular configuration which is to be treated with the required radiation dosage for the intended purpose. The target region may also be referred to, for example, as a dose contour.

As will become apparent hereinafter, the various features of the present invention are equally applicable to both stereotaxic radiosurgery and stereotaxic radiotherapy. However, for purposes of ease, the term stereotaxic radiosurgery will be used herein (both in the specification and appended claims) to refer to both stereotaxic radiosurgery and stereotaxic radiotherapy. Thus, for example, a radiosurgical beam recited herein is intended to refer to such a beam and also a radiotherapeutic beam.

As indicated above, the copending Adler patent application is incorporated herein by reference. As will be described in more detail hereinafter, each stereotaxic radiosurgical apparatus disclosed in the Adler application is designed to carry out radiosurgery on a particular target region within a patient utilizing previously obtained reference data, for example 3-dimensional mapping data, indicating the position of the target region with respect to its surrounding area which also contains certain nearby reference points, for example existing bone structure or implanted fiducials. In accordance with this procedure, means are provided for directing a radiosurgical beam of radiation into the target region. In order to ensure that this radiosurgical beam is accurately directed into the target region, a number of diagnostic beams of radiation, actually target locating beams, are directed into and through the surrounding area of the target region and the information derived from these latter beams of radiation is used along with the previously obtained reference data to accurately aim the radiosurgical beam into the target region. While this overall procedure is quite satisfactory for its intended purpose, the present invention provides for a number of improvements.

As will be described in more detail hereinafter, an apparatus is disclosed herein for carrying out stereotaxic radiosurgery (or radiotherapy) on a particular target region within a patient, especially a target region which is irregular in shape as contrasted with a typical spherically shaped target region. This apparatus, which is designed in accordance with the present invention, utilizes means for generating a radiosurgical beam of radiation and beam aiming means. The beam aiming means includes a robotic arm in a preferred embodiment and serves to support the beam generating means in a way which directs the radiosurgical beam along a beam path through the target region.

In accordance with one feature of the present invention, the radiosurgical apparatus disclosed herein includes means for moving the beam aiming means along a predetermined, non-circular and non-linear path transverse to the beam path while, at the same time, the beam path is directed into the target region. In this way, the radiosurgical beam can be directed through the target region from particular treatment points along the non-circular and non-linear path so as to define a specific nonspherical target region. In the actual embodiment disclosed herein, this predetermined, non-circular and non-linear transverse path is a specific spiral path which has been selected so that the non-spherical target region is in the shape of a specific ellipsoid. In this way, an irregular shaped tumor can be treated more effectively than heretofore possible by providing a target region or dose contour approximating but entirely surrounding the irregular shaped tumor. In the past, a tumor of this shape required a series of spherical dose contours which, in many cases, covered more or less of the tumor than necessary.

In a preferred, actual working embodiment of the apparatus disclosed herein, its beam aiming means includes a robotic arm which is free to move in at least three dimensions in order to follow the non-circular, non-linear transverse path recited immediately above. As a result, in accordance with a second feature of the present invention, in order to protect the patient, the apparatus is provided with emergency stop means separate from and independent of the beam aiming means and its robotic arm for automatically stopping all movement of the robotic arm and automatically turning off the radiosurgical beam if the robotic arm deviates from its intended non-circular, non-linear transverse path.

In addition to the features just discussed, the apparatus disclosed herein includes a unique procedure for ensuring that the radiosurgical beam is accurately directed into the target region at substantially any point in time during radiosurgery, that is, in substantially real time. Like the apparatus disclosed in the Adler application, the apparatus disclosed herein is provided with previously obtained reference data indicating the position of the target region with respect to its surrounding area which also contains certain nearby reference points. The disclosed apparatus, like Adler's, also utilizes a plurality of diagnostic or target locating beams of radiation to obtain substantially real time location data which is compared with the previously obtained reference data for determining the location of the target region in substantially real time. However, as will be described in more detail hereinafter, the apparatus disclosed herein carries out this target locating procedure in accordance with a unique, specific temporal sequence that allows the apparatus to function in a rapid but reliable manner.

The present invention will be described in more detail hereinafter in conjunction with the drawings, wherein:

FIG. 5 illustrates, in a view similar to FIG. 3, part of the arrangement found in FIG. 3 but modified to incorporate a feature of the present invention, specifically an arrangement for automatically stopping all movement of the robotic arm forming part of the arrangement shown in FIG. 3 in the event that the robotic arm deviates from its movement along a predetermined transverse path;

FIG. 6 illustrates, schematically, a block diagram corresponding to the emergency stop feature shown in FIG. 5;

Figure 3:
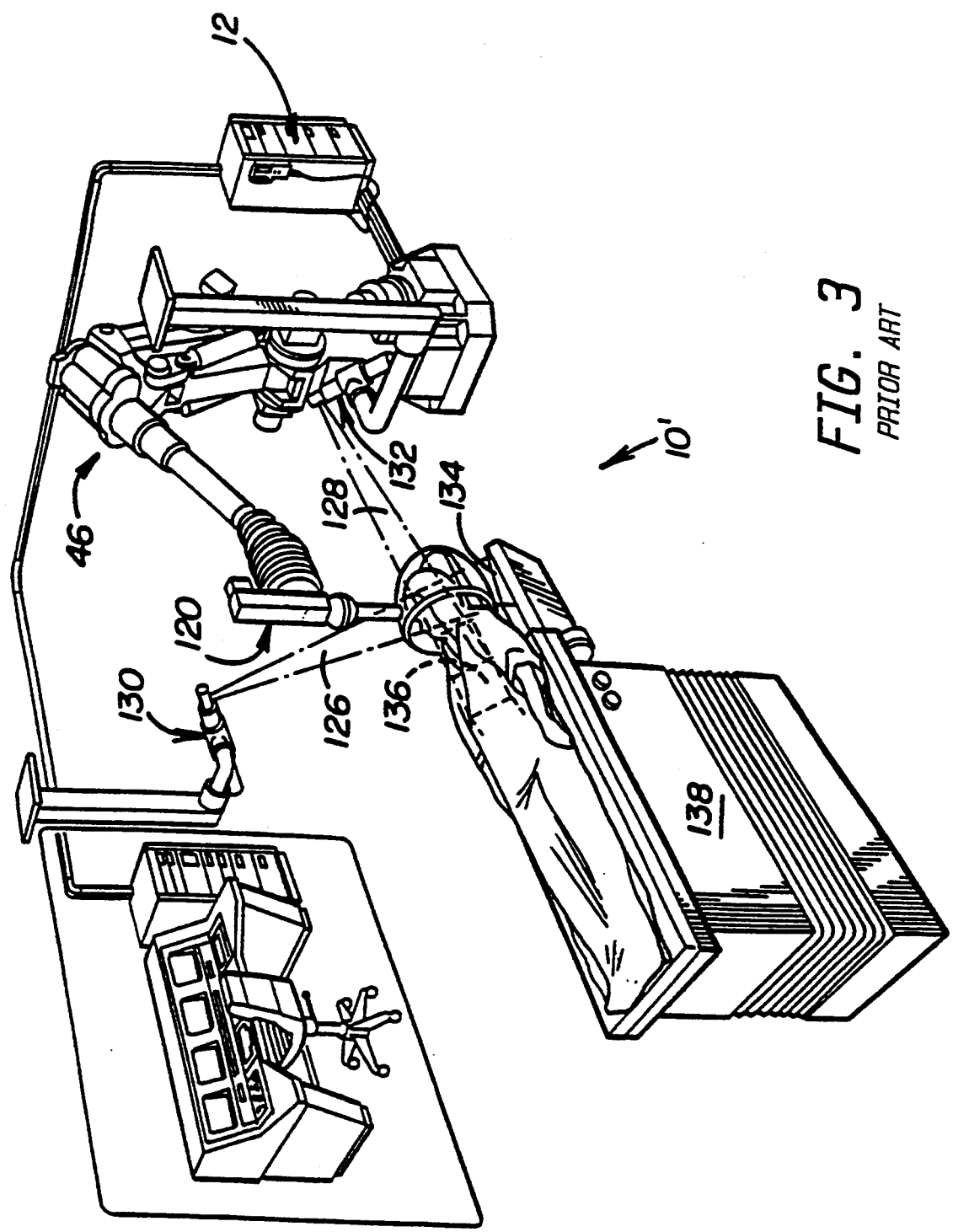
FIG. 3 illustrates, in a view similar to FIG. 1, an alternative embodiment of an apparatus described in the Adler application.

FIGS. 7 and 8 illustrate, diagrammatically, the way in which the robotic arm of the arrangement, as illustrated in FIG. 3, moves along a non-circular, non-linear path, specifically a spiral path, in order to provide a non-spherical target region more specifically a target region which is ellipsoid in shape; and FIG. 9 illustrates, diagrammatically, the way in which the apparatus are operated, temporally speaking, in accordance with the present invention.

Figure 1:
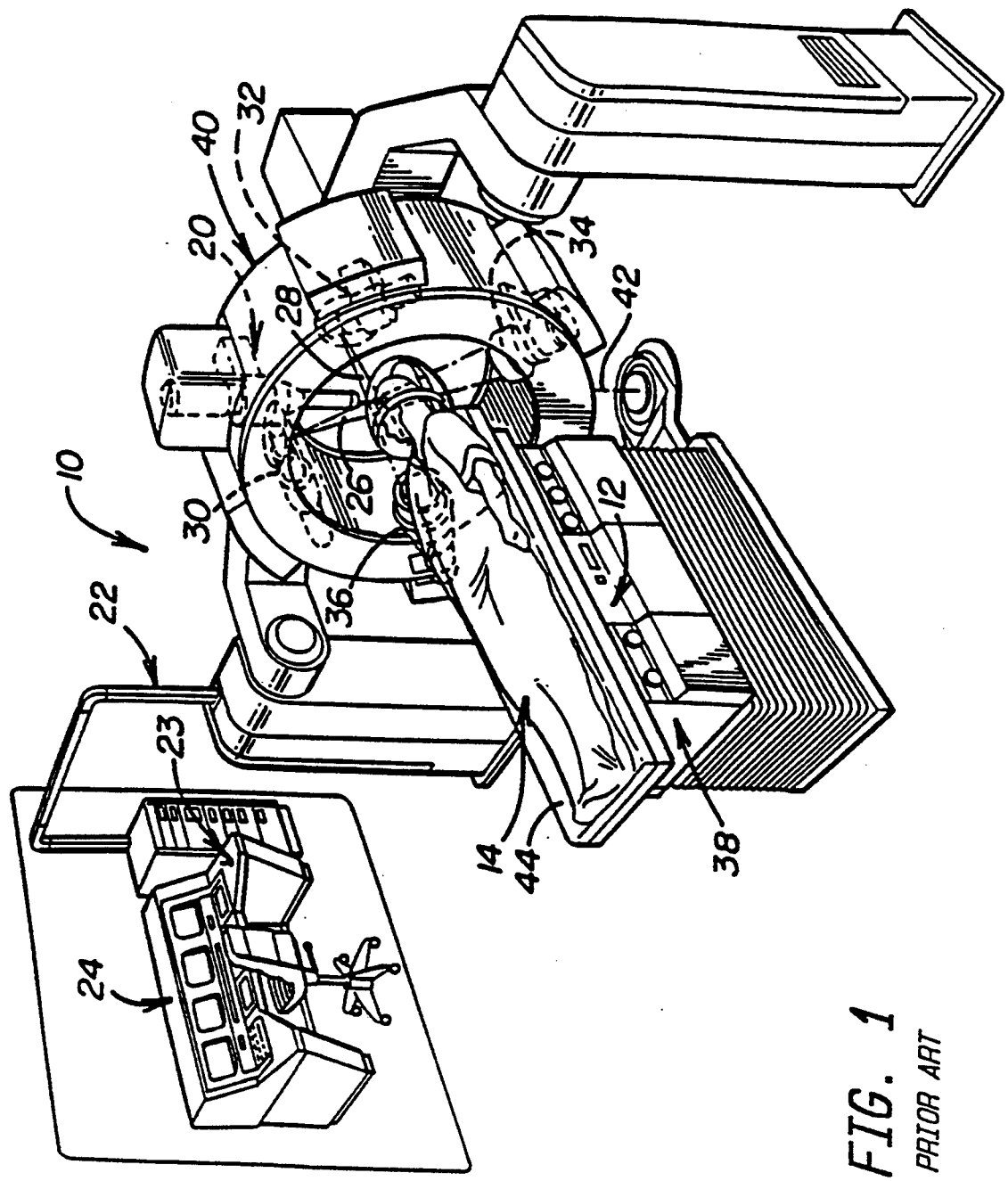
FIG. 1 illustrates, in isometric view, one embodiment of the apparatus described in the previously recited Adler copending patent application.

Turning now to the drawings, wherein like components are designated by like reference numerals throughout the various figures, attention is first directed to FIG. 1 which illustrates a stereotaxic radiosurgical apparatus designed in accordance with one embodiment of the present invention and generally indicated by the reference numeral 10. As indicated previously, the present invention is directed to a number of improvements in the stereotaxic radiosurgical apparatus described in the previously recited Adler patent application. Therefore, with particular regard to apparatus 10, most of the components making up this apparatus are identical to corresponding components of the apparatus illustrated in FIG. 1 of the Adler application. In order to more fully appreciate the various features of the present invention, these corresponding components will be discussed first.

Figure 2:
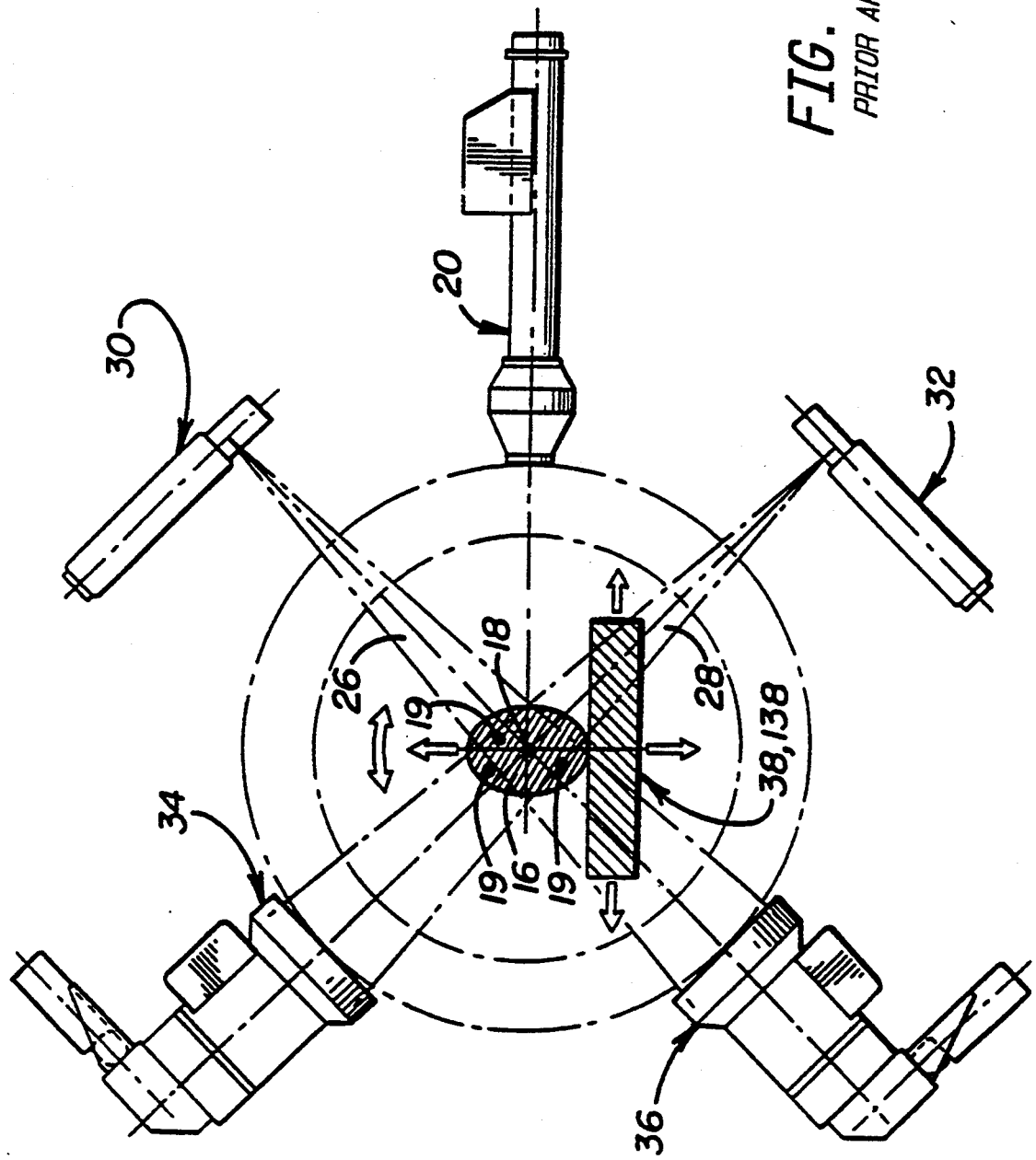
FIG. 2 illustrates, schematically, diagnostic X-ray imaging and accelerator focusing aspects of the Adler arrangement.
Figure 4:
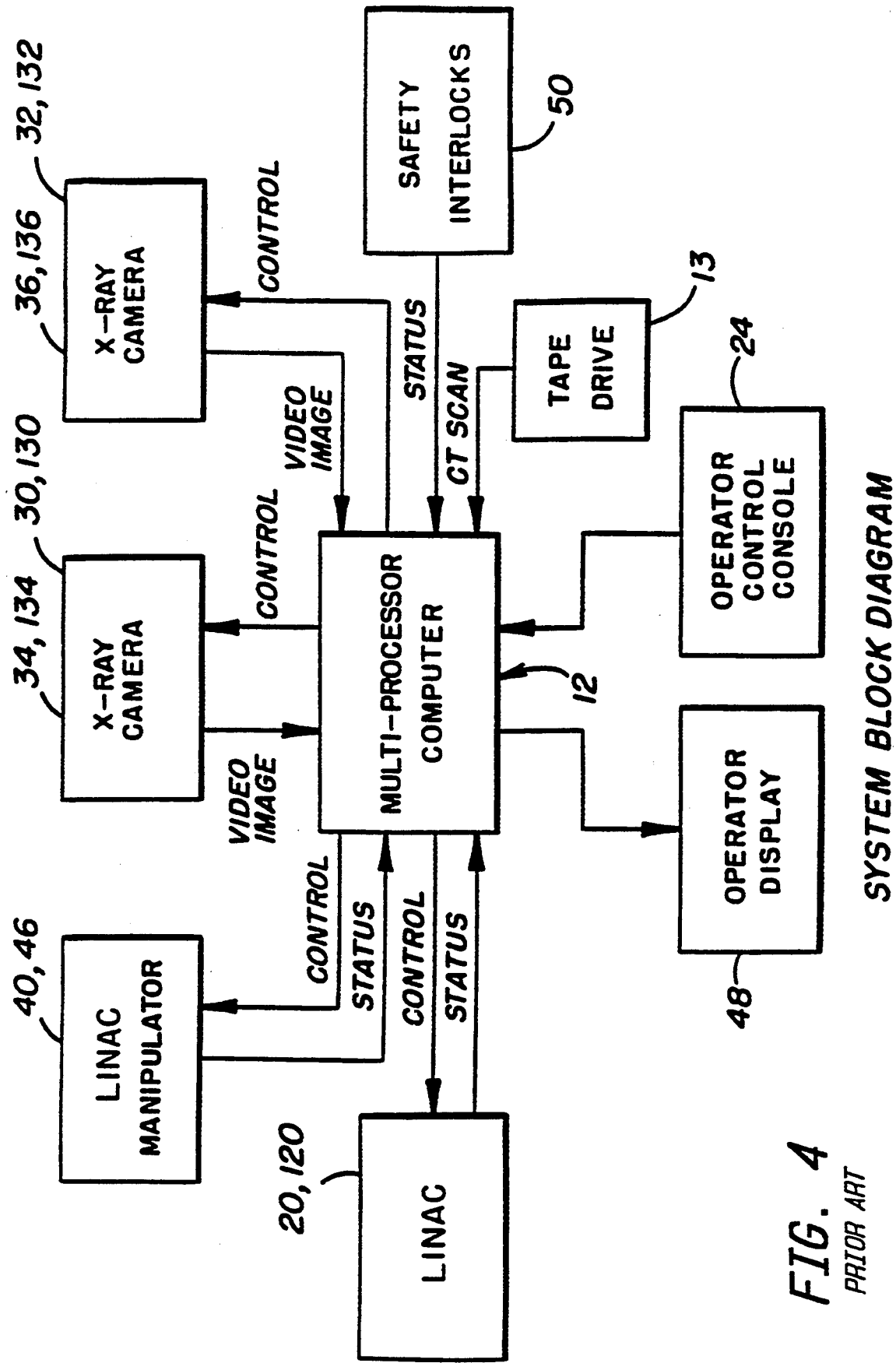
FIG. 4 illustrates, schematically, a system block diagram in accordance with both the Adler apparatus and the apparatus designed in accordance with the present invention.

As illustrated in FIG. 1, overall apparatus 10 includes data storage memory in, for example, a data processor such as a microprocessor 12 or in an auxiliary device such as a disk or a storage unit 13 (FIG. 4). The microprocessor 12 or the storage unit 13 has stored therein a 3-dimensional mapping of at least a portion of a living organism, i.e., of a patient 14. If the storage unit 13 is present, the 3-dimensional mapping data, normally in digital form, will generally be loaded into the microprocessor 12 for comparison purposes. The mapping covers a mapping region 16 (see FIG. 2) which includes and is larger than a target region 18 within the patient which is being selectively irradiated. The mapping region 16 of FIG. 2 is essentially the portion of the cranium 15 of the patient 14 so that bone structure is present to serve as an alignment reference. If desired, three or more fiducials 19 can be implanted, in which case it is not necessary to utilize bone structure as an alignment reference. This could be done for treatments of the brain but could be particularly desirable or necessary in less bony areas of the body.

The 3-dimensional mapping can be obtained by conventional techniques. For example a CAT scan (CT) can be utilized to obtain this image or magnetic resonance imaging (MRI) can be used to obtain this mapping. As is well known CT or computerized tomography operates through measurement of the differential absorption of X-ray beams and treats the resulting data by Fourier transforms. MRI utilizes the nuclear magnetic resonance property to obtain a 3-dimensional mapping. Apparatus for carrying out both procedures is available commercially. Furthermore, the data is available in digitized form whereby it can be readily stored in the memory unit 13 and/or in the microprocessor 12.

A beaming apparatus 20 is provided which, when activated, emits a collimated surgical ionizing beam of a strength sufficient to cause the target region 18 to become necrotic. One beaming apparatus which can be utilized is in the nature of a linear accelerator, preferably an X-ray linear accelerator, although other ionizing radiation sources could be used as can other ionizing radiations. Such X-ray apparatus is available commercially. It has also been described in a number of texts including "The Physics Of Radiology", 3rd Edition, 5th printing, by A. E. Johns and J. R. Cunningham, 1974, Charles C. Thomas, publisher, Springfield, Ill. A radio frequency wave is produced by a power supply, modulator and power tube and is fed into the accelerator 20 via a wave guide 22. The velocity of the wave increases as it passes down the tube.

Electrons can be given an energy of, for example, 6 Mev in a 2 meter long tube. The electrons can be impinged upon a target where X-rays are produced in a beam collimated in a desired direction. Such apparatus is available from various manufacturers including, for example, Varian. The preferred apparatus, an X-ray linear accelerator, preferred because of its relatively small size and relatively light weight, is manufactured by Schonberg Radiation Corporation of Santa Clara, Calif. and is marketed under the trademark MINAC.

On operator activation of a switch, for example, a switch 23 on a control console 24, the beaming apparatus 20 can be activated.

As illustrated in FIGS. 1 and 2, means are provided for passing first and second diagnostic or target locating beams 26 and 28 through the mapping region 16, the beams being laterally extensive sufficiently to provide projections of the mapping region. The first and second diagnostic beams 26 and 28 are at a known non-zero angle relative to one another. In the particular embodiment illustrated in FIGS. 1 and 2 the beams 26 and 28 are orthogonal to one another. However, any angle can be utilized so long as it is non-zero. Beams 26 and 28 are generated respectively by respective diagnostic X-ray generating apparatus 30 and 32. Image receivers 34 and 36, respectively, in the embodiment of FIGS. 1 and 2, image amplifiers, receive the beams 26 and 28 and pass the resulting electrical signals, with amplification if desired, to the microprocessor 112 where they are compared with the 3-dimensional mapping.

As is shown in FIG. 4, the image receivers 34 and 36 are connected to the microprocessor 12. The image receivers 34 and 36 can themselves provide digital signals or an A/D converter can be present as part of or in association with the microprocessor whereby images detected by the image receivers 34 and 36, which are representative of two different planar regions of the mapping region 16, can be compared in digital form with the 3-dimensional mapping (in digital form) of the mapping region 16. Utilizing conventional geometric calculation techniques the precise location of the target region 18 Which is to be irradiated is thereby fully known.

Means are provided for adjusting the relative positions of the beaming apparatus 20 and the patient 14 as needed in response to data which is representative of the real time location of the target region 18 in such a manner that the collimated beam, when activated, is continuously focused on to the target region 18. In the particular embodiment illustrated in FIG. 1, the means for adjusting the relative positions of the beaming apparatus and the patient comprises a gantry 40 to which the beaming apparatus 20, the diagnostic X-ray generators 30 and 32 and the image receivers 34 and 36 are mounted along with conventional apparatus for lowering and raising the operating table 38 and for rotating it about an axis 42 and for tilting the top 44 of the operating table 38 about a longitudinally extending axis, all as illustrated by arrows in FIG. 2. The broad range of adjustment of the relative positions of the gantry 40 and the patient 14 allows the collimated beam to be continuously focused on the target region while the healthy tissue through which the collimated beam passes is changed, as by rotating the beaming apparatus 20 through as much as 360° about the patient. Previous apparatus was limited to about 180° rotation. Generally, it is preferable to keep the: patient 14 relatively stationary and to move the gantry 40.

The foregoing discussion of apparatus 10 related to the components of that apparatus in common with the corresponding Adler apparatus (FIG. 1 in the Adler application). Before .discussing Applicant's improvements to apparatus 10, attention is directed to an alternative stereotaxic radiosurgical apparatus which is illustrated in FIG. 3 and generally designated by the reference numeral 10'. This particular apparatus corresponds in many respects to the stereotaxic radiosurgical apparatus illustrated in FIG. 3 in the Adler patent application. As was the case with apparatus 10, the similarities between apparatus 10' and the Adler apparatus will be discussed before the various improvements provided by applicant. At the outset, however, it should be noted that one primary difference between apparatus 10' and apparatus 10 illustrated in FIG. 1 is that the former does not utilize a gantry 40 and it is not necessary to move operating table 138. Rather, as will be seen, a beam generating device forming part of apparatus 10 is supported by means of a robotic arm movable in at least three dimensions.

Turning specifically to FIG. 3, apparatus 10' is shown including a beaming apparatus or generator 120 which is supported and positioned by a processor controllable robotic arm mechanism 46 having six axes of motion and six degrees of freedom (three translation and three rotation), whereby the beaming generator can be moved freely about the patient's body, up or down, longitudinally along the patient's body, or laterally along the patient's body. Such robotic arm mechanisms are commercially available from, for example, GMF Robotics of Santa Fe Springs, Calif., and are sold under the designation S-420F. Other such readily available robotics arm mechanisms are available from Adept Robotics, San Jose and Cincinnati Milicron. Utilizing such a mechanism, the radiation beam, which is collimated ionizing radiation beam, can be targeted on the site of treatment, that is, the target region, from substantially any desired direction. Thus, this embodiment allows the collimated beam to pass through any particular region of the healthy tissue for much less time than was the case with the prior art apparatus.

The means for passing first and second diagnostic beams 126 and 128 through the mapping region 18 in the FIG. 3 embodiment is in the nature of a pair of X-ray generators 130 and 132 which can be permanently mounted, for example, to the ceiling (not shown). Appropriate image receivers 134 and 136 serve to produce electronic images representative of the respective first and second images of the respective first and second projections within the mapping region 16 in the patient. The electronic images are passed to the microprocessor 12, going through an A/D converter if the images themselves are not already digital, whereupon comparison can take place. Signals are then generated by a second processor 12' (the controller for mechanism 46) which serves as a remote extension to multiprocessor 12 to control the positioning of the overall operation of the robotic arm mechanism including a mechanism whereby the; positioning of the beaming apparatus 120 is adjusted to assure that the collimated surgical beam which it produces is focused on the target region 18 that is to be irradiated. In FIG. 3, processor or controller 12' is shown separate and distinct from processor 12 since, in an actual embodiment, controller 12' forms part of the overall mechanism 46. However, the controller could be incorporated directly into processor 12. Thus, in the block diagram of FIG. 4, controller 12' could be depicted either as part of computer or processor 12, or as part of LINAC Manipulator 46 (which is the robotic mechanism 46 in FIG. 3).

FIG. 4 illustrates, in system block diagram form, operation of the logic by which the apparatus of FIG. 1 or FIG. 3 can be controlled. The 3-dimensional mapping, which covers a mapping region 16, is stored, for example, on tape in tape drive 13. Signals from the image; receivers 34,134 and 36,136 are passed to the processor 12. Control signals from the processor 12 are passed back to the image receivers 34,134 and 36,136 and/or the diagnostic x-ray generating apparatus 30,130 and 32,132 to activate them at desired time intervals or at operator command, all as indicated in FIG. 4. Signals from the processor 12 are passed to the robotic arm mechanism 46 (actually its controller 12') or to the gimbal 40 thus controlling its positioning with return signals from the gimbal 40 or robotic arm mechanism 46 indicative of positioning status being returned to the processor 12. The beaming apparatus 20,120 is normally activated by the processor 12 only when it is properly focused on the target region 18 and is normally otherwise not activated. However, it is possible to leave the beaming apparatus 20,120 on so long as exposure time of non-target regions in the patient 14 is sufficiently restricted so as to preclude radionecrosis of non-target tissue. The collimated beam can be retargeted on the target region from any selected direction thus providing the capability of irradiating from multiple directions. Operator controls are provided by the operator control console 24 which includes an operator display 48. Safety interlocks 50 are also provided for discontinuing operation of the processor 12 and of the beaming apparatus 20,120 in instances when such is necessary.

Basically, the image receivers 34,134 and 36,136 provide images which are separated in time by selected time intervals. These images are compared in the processor 12 with the CT scan which has generally been loaded into the processor 12 from the tape drive 13 and the positioning of the gimbal 40 or robotic arm mechanism 46 is adjusted, as necessary, to retain focussing of the collimated beam generated by the beaming apparatus 20,120 upon the target region 18 within the mapping region 16 in the patient. The gimbal 40 or the robotic arm mechanism 46 can desirably be moved either continuously or in steps while the collimated beam is kept focused upon the target region 18, thus minimizing the extent to which any healthy tissue in the path of the beam is exposed to ionizing radiation.

In general it should be noted that apparatus and method of the present invention can be utilized substantially anywhere on the body. In those regions where there is no bone present to provide necessary markers from which the target region 18 can be located it may be necessary to insert the three fiducials 19 so as to provide artificial landmarks. It is also possible to use one or two fiducials if they are shaped to provide directional indications of their spatial orientation and/or if enough bone is present to provide one or more partial landmarks. The use of fiducials may even be desirable in locations in the body where sufficient bone is present since the fiducials may provide a better or more precise system for locating the target region 18 which is to be irradiated.

Having described apparatus 10 and apparatus 10' to the extent that they correspond to each stereotaxic radiosurgical apparatus described in the copending Adler patent application, attention is now directed to a number of improvements to these apparatus provided by Applicant in accordance with the present invention. These improvements include (1) an emergency stop arrangement which is applicable to apparatus 10' and which is illustrated in FIGS. 5 and 6, (2) a unique technique for establishing a non-spherical target region 18 which is also especially applicable to apparatus 10', and (3) a unique temporal procedure for operating the radiosurgical beam and the diagnostic target locating beams in order to continuously locate the target region in substantially real time. This latter feature is applicable to both apparatus 10 and apparatus 10' and the relevant timing diagram is illustrated in FIG. 9.

Turning specifically to FIG. 5, processor controllable robotic arm mechanism 46 forming part of overall apparatus 10' is shown supporting beaming apparatus 120 over patient 136. The rest of the overall apparatus illustrated in FIG. 3 has been omitted from FIG. 5 for purposes of clarity. On the other hand, apparatus 10' is shown in FIG. 5 including three devices A, B and C which are fixedly mounted in spaced-apart relationship to one another on tower 200 which, itself, is fixedly mounted to the ceiling by suitable means, as indicated at 202. At the same time, at least three and preferably more than three devices 1, 2, 3 and so on of a different type are mounted on the rearward body 204 of generating apparatus 120 which, mechanically speaking, forms an extension of robotic arm 206 which, in turn, comprises part of overall robotic arm mechanism 46. Each of the devices A, B, and C serves as a combination transmitter/receiver alternatively transmitting coded infrared pulse signals and receiving back coded ultrasound pulse signals. On the otherhand, each of the devices 1, 2, 3 and so on serves as a receiver/transmitter which is specifically designed to receive uniquely coded infrared pulsed signal from each of the devices A, B and C and transmit back a correspondingly coded pulsed ultrasound signal. These various devices cooperate with one another in the manner to be described so as to continuously monitor the precise position and orientation of beam generating apparatus 120, and therefore the radiosurgical beam itself in order to shut down the apparatus if the beam deviates from its intended path. To this end, for reasons which will become apparent, apparatus 10' is provided with eight of these latter receiving/transmitting devices, devices 1, 2 and 3 mounted to the front face of body 204, devices 4 and 5 mounted on its side face, device 6 on its back face and two additional devices 7 and 8 mounted on the opposite side face of body 204, although not shown in FIG. 5.

Devices A, B and C and devices 1–8 form part of an overall emergency stop arrangement 208 which is illustrated diagrammatically in FIG. 6. As will be described hereinafter in conjunction with FIGS. 7 and 8, apparatus 10' is designed in accordance with a second feature of the present invention such that its beam generating apparatus 120, and therefore its beam, is intended to move along a predetermined, 3-dimensional path transverse to the path of the beam. The processor controllable robotic arm mechanism 46 and the multiprocessor computer 12 are designed to cooperate with one another in order to accomplish this. However, in the event of a computer error causing the beam generating apparatus 120 to deviate from its path, the patient could be placed in danger without a backup system for shutting down the apparatus under such circumstances. Arrangement 208 serves as that backup.

Emergency stop arrangement 208 not only includes the three fixedly mounted devices A, B and C and the devices 1–8 mounted for movement with beam generating apparatus 120, but also multiprocessor computer 12, as shown in FIG. 6. As the robotic arm 206 is caused to move the beam generating apparatus 120 along its intended path of movement, device A transmits infrared pulsed signals which are specifically coded to device 1. If device 1 is in the field of view of device A at that point in time, it will receive the signals and in response thereto transmit back a correspondingly coded pulsed ultrasound signal which is received by device A and processed through computer 12 with readily providable, conventional means using time of flight information to establish the position of device 1 with respect to device A at that instant. Thereafter, device A carries out the same procedure in cooperation with device 2 using coded infrared signals unique to device 2, and then device 3, device 4 and so on. After device A carries out a full sequence of position monitoring communications with the devices 1–8 (with devices B and C turned off), device A is turned off along with device C, and device B is caused to carry out the same procedure, and then device C (with devices A and B turned off).

Each of the devices A, B and C can only communicate with those Devices 1–8 that are within its field of view. In the case of overall arrangement 208, devices 1–8 are positioned such that, at any possible position of robotic arm 206, at least three of the devices 1–8 will always be in the field of view of the operating devices A, B or C. In that way, when the emergency stop arrangement 208 goes through one complete monitoring cycle (one full A-sequence, B-sequence and C-sequence), at least three points on the beam generating apparatus will have been located for each device A, B and C. With a suitable and readily providable algorithm within computer 12, this positional information is utilized to determine whether beam generating apparatus is, indeed, on its intended path of movement at that point in time or has deviated from its intended path. If the latter, the computer is interconnected with both the robotic arm mechanism 46 and the beam generating apparatus 120 for automatically shutting down the apparatus, that is, for at least automatically stopping movement of the robotic arm and turning off the radiosurgical beam. This is carried out entirely independent of the servo feedback relationship between the robotic arm mechanism 46 and its controller or processor 12' which is used as a primary means for guiding generating apparatus 120 along its intended path. In an actual embodiment, arrangement 208 continuously monitors the position of apparatus 120 during its movement by cycling through A, B and C monitoring sequences three times each second, as apparatus moves at a rate of 1 cm/sec to 5 cm/sec.

With particular regard to emergency stop arrangement 208, it is to be understood that the present invention is not limited to the particular positional relationship between the fixedly mounted devices A, B and C and the movable devices 1, 2, 3 and so on or the speed at which the arrangement cycles through its monitoring sequences. Nor is the present invention limited to the particular number of such devices or the particular devices used. Suitable cooperating devices can be readily provided in view of the teachings herein. In an actual working embodiment, each of the devices A, B and C ;and each of the devices 1, 2, 3 and so on are purchased from Litek Advanced Systems Ltd. through its distributors Celesco Transducers of Los Angeles, Calif. under Model No. VS-110PRO.

Having described emergency stop .arrangement 208, attention is now directed to FIGS. 7 and 8 which illustrate the second feature of the present invention, specifically a particular way in which processor controllable robotic arm mechanism 46 is operated by computer 12 to move beam generating apparatus 120 in a way which results in the creation of a non-spherical target region 18. As described previously, apparatus 10' is designed so that its beam generating device 120 can be moved by the robotic arm mechanism 46 along a predetermined path which is determined by the multiprocessor computer and which is transverse to the path of the radiosurgical beam while, at the same time, the beam path is directed into the target region. In radiosurgical apparatus designed heretofore, movement of its beam generating apparatus has been limited to specific predetermined arcs on a sphere intended to establish a spherical target region by directing the radiosurgical beam through the target region as it moved along those paths.

In accordance with the present invention, multiprocessor computer 12 is provided with an algorithm which operates the robotic arm mechanism 46 in a way which causes it to move the beam generating apparatus 120 along a predetermined, non-circular and non-linear path transverse to the beam path while, at the same time, the beam path is directed into the target region. In this way, the radiosurgical beam can be directed through the target region at specific treatment points along the non-circular and non-linear path so as to define a non-spherical target region. In an actual working embodiment of the present invention, computer 12 is provided with an algorithm which causes the beam generating apparatus to move through a particular spiral path which lies on the surface of a sphere, as illustrated in FIG. 7. The spiral path is generally indicated at 210 on the surface of sphere 212 which, in turn, has its center 214 at the origin of an X, Y, Z coordinate system. Target region 18 which is shown somewhat irregular and somewhat elongated in shape, rather than being spherical in shape, surrounds centerpoint 214.

In actual operation, beam generating device 120 is caused to move along spiral path 210 while constantly aiming its beam at point 214 within target region 18. The radiosurgical beam is moved intermittently staffing at, for example, the treatment point TP1 and thereafter moving to treatment point TP2, then TP3 and so on through the spiral path to the last treatment point TPN. The beam generating device directs its radiosurgical beam into the target region only at the various treatment points, and it does so in a stationary position. Between treatment points, the beam generating apparatus remains off. By selecting a specific spiral path 210 which will be described in detail hereinafter, and by selecting specific treatment points on the path, the beam generating apparatus can be made to provide a dose contour or target region 18' which is ellipsoidal in shape and which just surrounds the irregular shaped target region 18 as illustrated in FIG. 7. Specifically, as seen there, point 214 is at the center of symmetry of the ellipsoid which has its major axis extending along the Z axis and its minor axes extending along the X, Y axes. This ellipsoidal shaped dose contour is to be contrasted with the prior art which has heretofore been limited to spherical target regions. In the case of irregular, elongated region 18, several adjacent spherical target region, s would be required in order to irradiate this entire target region.

The spiral path 210 illustrated in FIG. 7 and episoidal shaped region 18' have been described within an X, Y, Z coordinate system which provides the necessary positional reference points for a particular algorithm that establishes spiral path 210 and treatment points TP1, TP2 and so on. In this regard, sphere 210 is duplicated in FIG. 8 along with the X, Y, Z axes. In addition, the radius R represents the radiosurgical beam path between centerpoint 214 and the output point of generating apparatus 120 (the point at which the radiosurgical beam is first generated). The angle $\theta$ corresponds to the angle between the Z axis and the beam path R while the angle $\phi$ is defined between the X axis and projection of beam path R on the X-Y plane. Based on these relationships, spiral path 210 may be defined by the following equations:

$$Z_i = R\cos \theta_i$$

$$X_i = R\sin \theta_i \cos \phi_i$$

$$Y_i = R\sin \theta_i \sin \phi_i$$

In each of the equations just recited, i corresponds to a particular treatment point on the curve. These treatment points may vary from application to application in order to customize the ellipsoidal target region. In one particular embodiment of the present invention, the treatment points are established by the following equations where N represents the; total number of treatment points:

$$\theta_i = \frac{\pi}{6} + \frac{\pi}{6} \cdot \frac{i}{N}$$

$$\phi_i = 2\pi \frac{5i}{N}$$

$$i = 0, 1, 2 \ldots, N$$

While the foregoing has been a specific description of how apparatus 10' can generate a particular ellipsoidal shaped target region by moving its beam generating apparatus along a specific spiral path, it is to be understood that the present invention is not limited to this particular application. Beam generating apparatus can be caused to move along any non-circular, non-linear path to establish a non-spherical target region in view of the teachings herein. For any given patient, a treatment planning strategy is established which includes determining the shape of the treatment volume, that is, the dose contour or target region and the amount of radiation, that is, the dose distribution, to be delivered inside that volume. In the case of curve 210, for example, the amount of radiation dose delivered to the ellipsoidal shaped target region can be varied by varying the radius R or by changing the strength of the radiosurgical beam. In most cases, minimizing R is preferable so as to minimize the shadow component of the radiosurgical beam. By changing the treatment points $TP_1$, $TP_2$ and so on, the ellipsoidal shape of the target region can be varied or customized. The present invention serves as a flexible working tool for establishing the best treatment planning strategy for each patient.

Having described the way in which apparatus 10' can be operated to establish a non-spherical target region by appropriately moving the robotic arm along a predetermined non-circular, non-linear path and the way in which the robotic arm can be automatically stopped by means of an independent emergency stop arrangement, attention is now directed to a unique way in which apparatus 10 and 10' are operated in order to ensure that their generating apparatus 20, 120 are constantly aimed toward the target region. As described previously, each apparatus 10, 10' carries out stereotaxic radiosurgery on a particular target region within a patient utilizing previously obtained reference data indicating the position of the target region with respect to its surrounding area which also contains certain nearby reference points. The apparatus also utilizes a pair of diagnostic beams of radiation or target locating beams, as they will be referred to in this discussion. These beams are passed through the surrounding area containing the target region and reference points and, after passing through the surrounding area, contain data indicating the positions of the reference points within the surrounding area. This position data is collected by cooperating detectors, as described previously, and delivered to the multiprocessor computer where the latter compares it with previously obtained reference data for determining the position of the target region with respect to each of the reference points during each such comparison. The radiosurgical beam is accurately directed into the target region in substantially real time based on this information.

In accordance with a further feature of the present invention, the various steps just described to ensure; that the radiosurgical beam is always directed into the target region are carried out in a specific temporal order, as illustrated in FIG. 9. The TREATMENT period set forth there refers to a period during which the beam generating device 20 or 120 is stationary and its beam is on. The target locating period refers to the period between treatment periods and includes a first subperiod in which the target locating devices are on so as to generate location data, a second subperiod during which the location data is compared with the previously obtained reference data, and finally a third subperiod during which the beam generating device positions the beam, if necessary, to ensure 1:hat the beam is directed into the target based on the last comparison. Note specifically that the first subperiod, the second subperiod and the third subperiod making up the overall target locating period immediately follow one another and that the target locating period immediately follows a treatment period. During the target locating period, the beam generating device is caused to move along its transverse path of movement from one treatment point to another. In an actual working embodiment of 1:he present invention, each treatment period is between about 0.5 and 1 second in duration and each of the target locating periods is between about 1 and 2 seconds in duration periods. Thus, generating device 20 or 120 is turned on and off every second or two during operation of the overall apparatus.

While the present invention has been described in connection with specific embodiment thereof, it will be understood that it is capable of further modification, and this application is intended to cover any variations, uses, or adaptations of the invention following, in general, the principles of the invention including such departures from the present disclosure has within known or customary practice in the art to which the invention pertains and as may be applied to the essential features hereinbefore set forth, and as fall within the scope of the invention and limits of the appended claims.

I claim:

1. An apparatus for carrying out stereotaxic surgery on a particular target region including a target and indicating a position of the target region with respect to a surrounding area also containing certain nearby reference points each having a location, said apparatus comprising:
   (a) a radiation beam generator including a delivery mechanism;
   (b) means for generating target locating beams;
   (c) first means for intermittently directing a radiosurgical beam of radiation along a beam path into the target region;
   (d) second means for intermittently directing a plurality of target locating beams of radiation into and through the surrounding area containing the target region and reference points so that the target locating beams, after passing through the surrounding area, contain location data indicating the locations of the reference points within the surrounding area;
   (e) third means responsive to said intermittently directed target locating beams (i) for obtaining the location data from said target locating beams, (ii) for intermittently comparing the location data so obtained with the previously obtained reference data, and (iii) for determining from each of the intermittent comparisons a position of the target region with respect to the locations of the reference points as a result of each such comparison;
   (f) fourth means for operating said first, second and third mentioned means in cooperation with one another (i) such that said radiosurgical beam is directed into said target region only during intermittent treatment periods and alternatively therewith, said target locating beams are directed through said surrounding area only during intermittent target locating periods and (ii) such that, during each target locating period, the most recently obtained location data from said locating beams is used during that period to compare the location data with the reference data and determine the position of the target with respect to the locations of the reference points;

(g) fifth means operable within each target locating period and responsive to the position of the target region determined by said third means within that period for insuring that said radiosurgical beam is accurately directed into said region;

wherein said first means includes means for moving said radiosurgical beam along a predetermined path transverse to said beam path while, at the same time, the radiosurgical beam path is directed into said target region, whereby to cause the radiosurgical beam to pass through different sections of healthy tissue as a result of its transverse movement along said predetermined path;

further comprising means for providing that said transverse path is a non-circular, non-linear path, whereby movement of said radiosurgical beam along said non-circular, non-linear path defines a non-spherical target region;

wherein said means for moving said radiosurgical beam along said non-circular, non-linear transverse path includes a robotic arm which carries said delivery mechanism of said radiation beam generator, said apparatus also including emergency stop means separate from and independent of said first means for automatically stopping all movement of and turning off said radiosurgical beam if said radiosurgical beam deviates from said transverse path of movement;

wherein said emergency stop means includes fixedly moused signal transmitting/receiving means mounted to a fixed surface other than said robotic arm for transmitting and receiving signals, movable signal transmitting/receiving means mounted to said robotic arm having a different position at different times for movement therewith and in signal communication with said fixedly mounted signal transmitting/receiving means, and means for cooperating with said fixedly mounted transmitting/receiving means and for continuously monitoring the position at a given time of said robotic arm and said radiation beam generator delivery mechanism; and wherein said fixedly mounted signal transmitting/receiving means includes a plurality of first devices, each of which including means for transmitting coded infrared signals and including means for receiving coded ultrasound signals, and wherein said movable signal transmitting/receiving means includes a plurality of second devices, each of which including means for transmitting coded ultrasound signals and including means for receiving coded infrared signals.

2. An apparatus according to claim 1 further comprising means for providing that each of said intermittent treatment periods is immediately followed by at least one of said target locating period.

3. An apparatus according to claim 2 further comprising means for providing that each of said treatment periods is between about 0.5 and 1.0 second in duration and each of said target locating periods is between about 1.0 and 2.0 seconds in duration.

4. An apparatus according to claim 1 further comprising means for providing that said means for moving said radiosurgical beam along said predetermined path does so only during target locating periods.

5. An apparatus according to claim 1 further comprising means for providing that said transverse path is circular or partially circular path having a center with said target region at the center thereof.

6. An apparatus according to claim 1 further comprising means for providing that said traverse path is a particular spiral path along which said radiosurgical beam is moved to define an ellipsoidal target region.

7. An apparatus for carrying out radiosurgery on a particular target region within a patient, said apparatus comprising:

(a) means for generating a radiosurgical beam of radiation;

(b) beam aiming means for supporting said beam generating means in a way which directs said beam along a beam path through the target region;

(c) means for moving said beam aiming means along a predetermined, non-circular and non-linear path transverse to said beam path while, at the same time, said beam path is directed into the target region, whereby directing said radiosurgical beam through said target region at particular treatment points along said non-circular and non-linear path defines a non-spherical target region; and further including means for generating a computed imaginary sphere having a surface and having a center within said target region and further comprising means for providing that said means for moving the beam aiming means does so in a way which causes the point at which said beam is generated to move along said transverse path which said transverse path at all time remains on said surface of said imaginary sphere.

8. An apparatus according to claim 7 further comprising means for providing that said predetermined particular spiral path along which said radiosurgical beam is moved to define an ellipsoidal target region.

9. An apparatus according to claim 7 including means for providing that said predetermined path is a particular spiral path on the surface of said sphere having a radius defined by the following equations:

$$Z_i = R\cos\theta_i$$

$$X_i = R\sin\theta_i \cos\phi_i$$

$$Y_i = R\sin\theta_i \sin\phi_i$$

where R is a radius of said sphere, X, Y and Z for a three dimensional coordinate system with a origin at the center of the sphere, $\theta$ is an angle defined by the Z axis and the radius R, $\phi$ is a angle defined by the X-axis and the X-Y component of the radius R within in the X-Y plane, and i is a particular treatment point on the spiral path.

10. An apparatus according to claim 9 further including means for moving said beam aiming means intermittently along said spiral path so that said beam is generated at said particular treatment point only when said beam aiming means is stationary.

11. An apparatus according to claim 10 including means for providing that there are a plurality of points i on said spiral path at which said beam is generated is defined by the following equations:

$$\theta_i = \frac{\pi}{6} + \frac{\pi}{6} \cdot \frac{i}{N}$$

$$\phi_i = 2\pi \frac{5i}{N}$$

$$i = 0,1,2\ldots,N$$

where N equals points in total i at which the beam is generated.

12. An apparatus according to claim 7 including emergency stop means separate from and independent of said beam aiming means for automatically stopping all movement of said beam aiming means and turning off said radiosurgical beam if said beam aiming means deviates from said transverse path.

13. An apparatus according to claim 12 further including a robotic arm wherein said emergency stop means includes fixedly mounted signal transmitting/receiving means mounted to a fixed surface other than said robotic arm for transmitting and receiving signals, movable signal transmitting/receiving means mounted to said robotic arm having a different position at different times for movement therewith and in signal communication with said fixedly mounted signal transmitting/receiving means, and means for cooperating with said fixedly mounted transmitting/receiving means and for continuously monitoring the position at a given time of said robotic arm and said radiosurgical beam generating means.

14. An apparatus according to claim 13 wherein said fixedly mounted signal transmitting/receiving means includes a plurality of first devices, each of which including means for transmitting coded infrared signals and including means for receiving coded ultrasound signals, and wherein said movable signal transmitting/receiving means includes a plurality of second devices, each of which including means for transmitting coded ultrasound signals and including means for receiving coded infrared signals.

15. An apparatus according to claim 7 including means for providing that said means for generating said radiosurgical beam does so in a controlled intermittent manner so as not to direct said beam into certain critical areas of the patient as the beam is moved along said transverse path.

16. An apparatus for carrying out radiosurgery on a particular target region within a patent, said arrangement comprising:
 (a) means for generating a radiosurgical beam of radiation;
 (b) means including a robotic arm for supporting said beam generating means in a way which directs said beam along a beam path through said target region;
 (c) means for moving said robotic arm and therefore said radiosurgical beam along a predetermined path transverse to said beam path while, at the same time, said beam path is directed into said target region; and
 (d) emergency stop means separate from and independent of said means including said robotic arm for automatically stopping all movement of said robotic arm and turning off said beam if said robotic arm deviates from said transverse path;

wherein said emergency stop means includes fixedly mounted signal transmitting/receiving means mounted to a fixed surface other than said robotic arm for transmitting and receiving signals, movable signal transmitting/receiving means mounted to said robotic arm having a different position at different times for movement therewith and in signal communication with said fixedly mounted signal transmitting/receiving means, and means for cooperating with said fixedly mounted transmitting/receiving means and for continuously monitoring the position at a given time of said robotic arm and said radiosurgical beam generating means; and wherein said fixedly mounted signal transmitting/receiving means includes a plurality of first devices, each of which including means for transmitting coded infrared signals and including means for receiving coded ultrasound signals, and wherein said movable signal transmitting/receiving means includes a plurality of second devices, each of which including means for transmitting coded ultrasound signals and including means for receiving coded infrared signals.

17. An apparatus according to claim 16 wherein said plurality of first devices includes three such devices and wherein said plurality of second devices includes a number of such devices sufficient to insure that each of said first devices is always in signal communication with at least three of said plurality of said second devices.

18. A method of carrying out stereotaxic surgery on a particular target region having a position within a patient utilizing previously obtained reference data indicating the position of said target region with respect to its surrounding area which also contains certain nearby reference points, each of which having a location said method comprising:
 (a) generating a radiation beam;
 (b) generating target locating beams;
 (c) intermittently directing a radiosurgical beam of radiation into said target region;
 (d) intermittently directing a plurality of target locating beams of radiation into and through the surrounding area containing said target region and reference points so that the target locating means, after passing through the surrounding area, contain location data indicating said locations of said reference points within the surrounding area, thus providing a plurality of target positioning periods;
 (e) in response to said intermittently directed target locating beams (i) for obtaining the location data from said target locating beams, (ii) intermittently comparing the location data so obtained with the previously obtained reference data, and (iii) determining from each of the intermittent comparisons the position of the target region with respect to said locations of the reference points as a result of each such comparison;
 (f) carrying out steps (c), (d) and (e) in cooperation with one another (i) such that said radiosurgical beam is directed into said target region only during intermittent treatment periods and alternatively therewith, said target locating beams are directed through said surrounding area only during intermittent target locating periods and (ii) such that, during each target locating period, the most recently obtained location data from said locating beams is used during that period to compare the location data with the reference data and determine the position of the target with respect to said location of the reference points; and (g) during said target locating period and responsive to the most recently determined position of the target region within that period, insuring that said radiosurgical beam is accurately directed into said region.

19. A method according to claim 18 including operating said method according to steps (a) through (f) so that each of said intermittent treatment periods is immediately followed by one of said target positioning periods.

20. A method of carrying out radiosurgery on a particular target region within a patient, said method comprising:

(a) generating a radiosurgical beam of radiation at a point by means of a beam generating device;

(b) supporting said beam generating device in a way which directs said beam along a beam path through said target region;

(c) moving said beam device along a predetermined, non-circular and non-linear path transverse to said beam path while, at the same time, said beam path is directed into said target region, whereby directing said radiosurgical beam through said target region at particular treatment points along said non-circular and non-linear path defines a non-spherical target region; and further including the step of generating a computed imaginary sphere having a surface and having a center within said target region and providing the step of moving said beam generating device in a way which causes the point at which said beam is generated to move along said transverse path while said transverse path at all times remains on said surface of said imaginary sphere having said center within said target region.

21. A method according to claim 20 further including providing that said predetermined path is a particular spiral path on the surface of said sphere defined by the following equations:

$$Z_i = R\cos\theta_i$$

$$X_i = R\sin\theta_i \cos\phi_i$$

$$Y_i = R\sin\theta_i \sin\phi_i$$

where R is a radius of said sphere, X, Y and Z for a three dimensional coordinate system with a origin at the center of the sphere, $\theta$ is an angle defined by the Z axis and the radius R, $\phi$ is a angle defined by the X-axis and the X-Y component of the radius R within in the X-Y plane, and i is a particular point on the spiral path.

22. A method according to claim 21 further comprising the step of intermittently moving said beam generating device along said spiral path and generating said beam therefrom only when said beam generating device is stationary.

23. A method according to claim 22 further including providing that the points i on said spiral path at which said beam is generated is defined by the following equations:

$$\theta_i = \frac{\pi}{6} + \frac{\pi}{6} \cdot \frac{i}{N}$$

$$\phi_i = 2\pi \frac{5i}{N}$$

$$i = 0,1,2\ldots,N$$

where N equals points i in total at which the beam is generated.

24. A method according to claim 20 further including providing that said predetermined path is a particular spiral path along which said radiosurgical beam is moved in order to define a target region that is ellipsoid in shape.

* * * * *